United States Patent
Howard et al.

(10) Patent No.: US 12,171,484 B2
(45) Date of Patent: Dec. 24, 2024

(54) SAFETY DEFAULT RETURN PATH FOR ELECTRIC FIELD THERAPY

(71) Applicant: Medtronic, Inc., Minneapolis, MN (US)

(72) Inventors: Brian T. Howard, Minneapolis, MN (US); Mark T. Stewart, Lino Lakes, MN (US); Lars M. Mattison, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 198 days.

(21) Appl. No.: 17/246,766

(22) Filed: May 3, 2021

(65) Prior Publication Data
US 2021/0369340 A1 Dec. 2, 2021

Related U.S. Application Data

(60) Provisional application No. 63/030,413, filed on May 27, 2020.

(51) Int. Cl.
*A61B 18/14* (2006.01)
*A61B 18/00* (2006.01)
*A61B 18/12* (2006.01)

(52) U.S. Cl.
CPC ...... *A61B 18/1492* (2013.01); *A61B 18/1206* (2013.01); *A61B 2018/00577* (2013.01);
(Continued)

(58) Field of Classification Search
CPC ............ A61B 18/1492; A61B 18/1206; A61B 2018/00577; A61B 2018/00613; A61B 2018/126; A61B 2018/00166
See application file for complete search history.

(56) References Cited

U.S. PATENT DOCUMENTS

| 4,974,048 | A  | 11/1990 | Chakravorty et al. |
| 6,321,114 | B1 | 11/2001 | Nutzman et al. |

(Continued)

FOREIGN PATENT DOCUMENTS

| WO | WO-2016065263 A1 * | 4/2016 | ............. A61N 1/056 |
| WO | 2018208795 A1 | 11/2018 | |
| WO | 2020026217 A1 | 2/2020 | |

OTHER PUBLICATIONS

International Search Report and Written Opinion dated Sep. 16, 2021, for corresponding International Application No. PCT/US2021/033534; International Filing Date: May 21, 2021 consisting of 11-pages.

*Primary Examiner* — Linda C Dvorak
*Assistant Examiner* — Abigail Bock
(74) *Attorney, Agent, or Firm* — Michael Best & Friedrich LLP

(57) ABSTRACT

A medical device including a catheter having a proximal portion and a distal portion. A plurality of electrodes is disposed along the distal portion, the plurality of electrodes including a first electrode pair having a first fixed polarity and a second electrode pair having a second fixed polarity different than the first fixed polarity. A first lumen extends through the distal portion, the first lumen includes a first conductor configured to connect to a first electrode of the first electrode pair and a second conductor configured to connect to a second electrode of the first electrode pair. A second lumen extends through the distal portion and separated from the first lumen, the second lumen includes a third conductor configured to connect to a first electrode of the second electrode pair and a fourth conductor configured to connect to a second electrode of the second electrode pair.

8 Claims, 4 Drawing Sheets

(52) U.S. Cl.
CPC .............. *A61B 2018/00613* (2013.01); *A61B 2018/126* (2013.01)

(56) References Cited

U.S. PATENT DOCUMENTS

| | | |
|---|---|---|
| 8,318,337 B2 | 11/2012 | Yokoyama et al. |
| 9,308,039 B2 | 4/2016 | Azure |
| 9,314,299 B2 | 4/2016 | Fang |
| 2003/0212394 A1 | 11/2003 | Pearson et al. |
| 2009/0318849 A1* | 12/2009 | Hobbs .................... A61N 1/327 606/41 |
| 2012/0150172 A1* | 6/2012 | Ortiz ................. A61B 18/1477 606/41 |
| 2013/0123778 A1* | 5/2013 | Richardson ........ A61B 18/1492 606/41 |
| 2013/0304062 A1 | 11/2013 | Chan et al. |
| 2018/0214195 A1 | 8/2018 | Fraasch et al. |
| 2019/0001143 A1* | 1/2019 | Sasaki .................. A61N 1/0563 |
| 2019/0223948 A1 | 7/2019 | Stewart et al. |
| 2019/0254735 A1 | 8/2019 | Stewart et al. |
| 2020/0129234 A1 | 4/2020 | Schultz |

\* cited by examiner

SAFETY DEFAULT RETURN PATH FOR ELECTRIC FIELD THERAPY

CROSS-REFERENCE TO RELATED APPLICATION

This application claims the benefit of U.S. Provisional Application Ser. No. 63/030,413 filed May 27, 2020.

FIELD

The present technology is generally related to safety features for medical devices, and in particular, safety features for medical devices delivering electric field therapy.

BACKGROUND

A broken wire may occur during normal catheter operation, such as during cardiac ablation therapy. There is a series of potential undesirable outcomes associated with initiating a delivery of voltage-based therapy when only one pole of the electric potential is exposed to the target area as a result of the broken wire. These potential outcomes including shock, atrial/ventricular fibrillation, embolic formation, and unintended stimulation which has the potential to harm both patients and operators. Moreover, ablation devices may have numerous electrodes and each electrode may be coupled to a common conductor and this increases the risk of an open or short circuit.

SUMMARY

The techniques of this disclosure generally relate to safety features for medical devices delivering electric field therapy.

In one aspect, the present disclosure provides a medical device including a catheter having a proximal portion and a distal portion. A plurality of electrodes is disposed along the distal portion, the plurality of electrodes including a first electrode plurality having a first fixed polarity and a second electrode plurality having a second fixed polarity different than the first fixed polarity. In a simplified illustration, the plurality of electrodes may at a minimum compose pairs of conducting electrodes. A first lumen extends through the distal portion, the first lumen includes a first conductor configured to connect to a first electrode of the first electrode pair and a second conductor configured to connect to a second electrode of the first electrode pair. A second lumen extends through the distal portion and separated from the first lumen, the second lumen includes a third conductor configured to connect to a first electrode of the second electrode pair and a fourth conductor configured to connect to a second electrode of the second electrode pair.

In another aspect of this embodiment, the lumens have electrically insulative properties.

In another aspect of this embodiment, the first electrode pair and the second electrode pair are configured to deliver high voltage electroporation energy.

In another aspect of this embodiment, the device further includes a guidewire lumen extending through the distal portion.

In another aspect of this embodiment, the first lumen and the second lumen are disposed on opposite sides of the guidewire lumen.

In another aspect of this embodiment, the first electrode of the second electrode pair is disposed between the first electrode and the second electrode of the first electrode pair.

In another aspect of this embodiment, the second electrode of the second electrode pair is disposed distal to the second electrode of the first electrode pair.

In another aspect of this embodiment, the first lumen is parallel to the second lumen.

In another aspect of this embodiment, the device further includes a guidewire lumen extending through the distal portion, and wherein the guidewire lumen is parallel to both the first lumen and the second lumen.

In one aspect, a medical device includes a catheter having a proximal portion and a distal portion. A first plurality of electrodes is disposed along the distal portion, the first plurality of electrodes including a first electrode and a second electrode distal to the first electrode, the first plurality of electrodes having a first fixed polarity; the first electrode having a higher resistance than the second electrode. A second plurality of electrodes is disposed between the first electrode and the second electrode, the second plurality of electrodes having a second fixed polarity different than the first fixed polarity.

In another aspect of this embodiment, the second electrode is disposed at a distal end of the catheter.

In another aspect of this embodiment, the second plurality of electrodes includes at least three electrodes.

In another aspect of this embodiment, a spacing between a distal most electrode of the second plurality of electrodes and the second electrode is less than a spacing between a proximal most electrode of the second plurality of electrodes and the first electrode.

In another aspect of this embodiment, the second electrode is larger than the first electrode.

In another aspect of this embodiment, the first plurality of electrodes and the second plurality of electrodes are configured to deliver high voltage electroporation energy.

In another aspect of this embodiment, in the event of a short circuit in the second electrode during operation of the device, high voltage electroporation energy is transmitted in a bipolar manner between the first electrode and the second plurality of electrodes.

In one aspect, a medical device includes a catheter having a proximal portion and a distal portion. A first electrode has a first fixed polarity disposed at a distal end of the catheter. A first plurality of conductors is connected to the first electrode and extends through the catheter. At least one second electrode is disposed proximal to the first electrode and has a second fixed polarity different than the first fixed polarity. A second plurality of conductors is connected to the at least one second electrode and extends through the catheter.

In another aspect of this embodiment, the at least one second electrode includes three electrodes.

In another aspect of this embodiment, the first electrode and the at least one second electrode are configured to deliver high voltage electroporation energy.

In another aspect of this embodiment, the first electrode and the at least one second electrode operate in bipolar mode during operation.

In another aspect of this embodiment the first electrode and the at least one second electrode are evenly spaced along the catheter.

In one aspect a medical system includes a source generator and control system capable of delivering opposing polarities to electrode elements located on one or more in-dwelling devices. The control system is configured to deliver a first polarity to a first electrode through independent and redundant conductive pathways and deliver a second polarity to a plurality of electrodes through independent conductive pathways.

In another aspect of this embodiment, one or more of the plurality of second electrodes has redundant independent conduction pathways from the source polarity.

In one aspect, a medical system includes a source generator and control system configured to deliver opposing polarities to electrode elements located on one or more in-dwelling devices. The control system is configured to deliver a polarity to a plurality of electrodes through independent conductive pathways.

In one aspect, a medical system includes a source generator and control system configured to deliver opposing polarities to electrode elements located on one or more in-dwelling device. The control system is configured to deliver a first polarity to at least one first electrode, deliver a second polarity to at least one second electrode, and deliver the first polarity to at least one third electrode through a conductive pathway with significantly larger impedance than that of the at least one first electrode.

In another aspect of this embodiment, the at least one third electrode includes one or more electrodes that can be engaged by the control system as either the at least one first electrode or the at least one second electrode.

In another aspect of this embodiment, the impedance magnitude of the source generator to a conductive electrode pathway during application of the polarity of the at least one third electrode is between 1.1 and 100 times larger than the impedance magnitude of the source to electrode polarity of the at least one first electrode.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
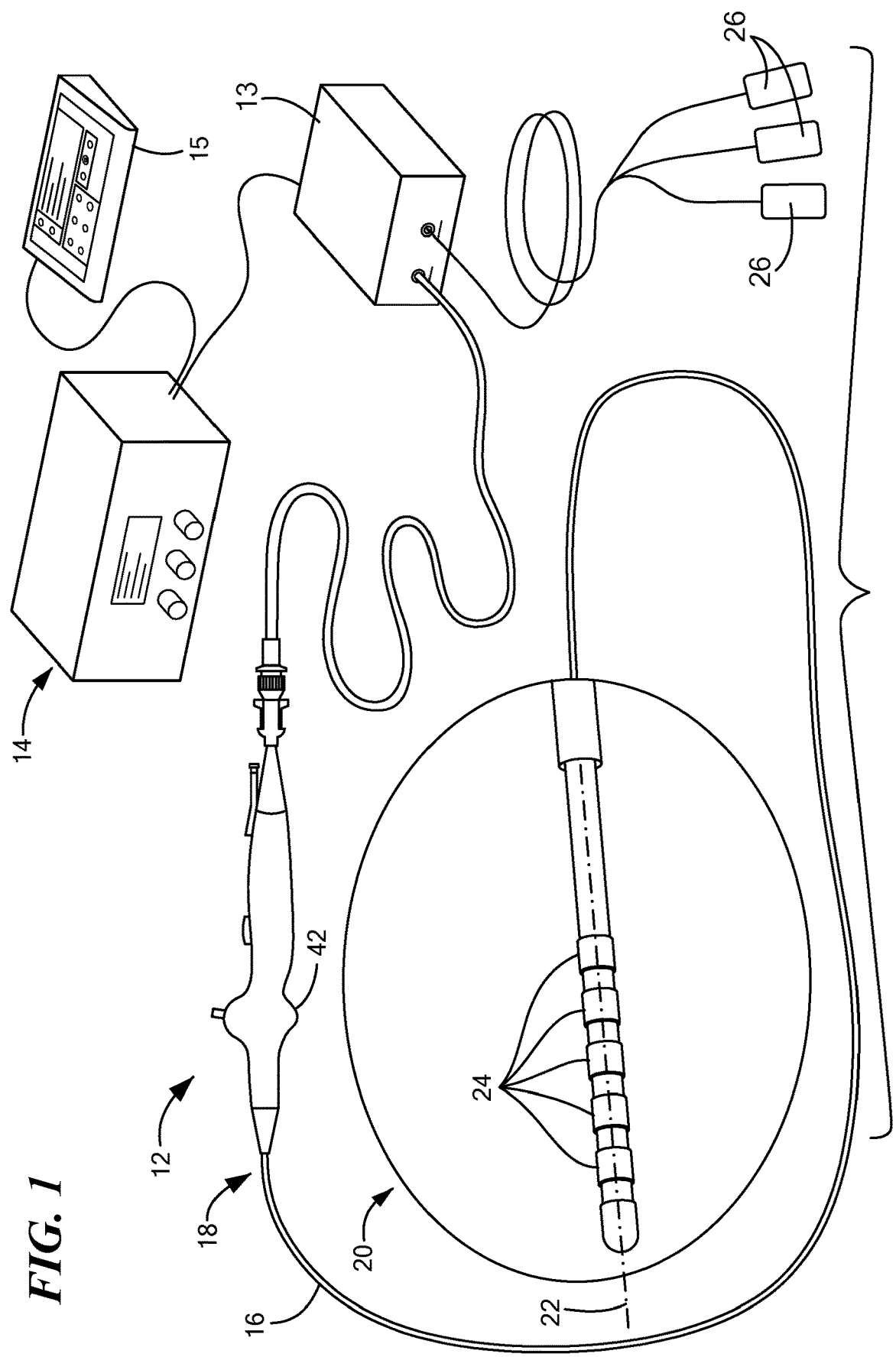
FIG. 1 is an assembly view of a medical system constructed in accordance with the principles of the present application.

Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled directly to an energy supply, for example, a pulse field ablation generator 14 including an energy control, delivering, and monitoring system or indirectly through a catheter electrode distribution system 13. A remote controller 15 may further be included in communication with the generator for operating and controlling the various functions of the generator 14. The medical device 12 may generally include one or more diagnostic or treatment regions for energetic, therapeutic and/or investigatory interaction between the medical device 12 and a treatment site. The treatment region(s) may deliver, for example, pulsed electroporation energy or radiofrequency energy to a tissue area in proximity to the treatment region(s).

The medical device 12 may include an elongate body or catheter 16 passable through a patient's vasculature and/or positionable proximate to a tissue region for diagnosis or treatment, such as a catheter, sheath, or intravascular introducer. The elongate body or catheter 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16. The distal portion 20 may generally define the one or more treatment region(s) of the medical device 12 hat are operable to monitor, diagnose, and/or treat a portion of a patient. The treatment region(s) may have a variety of configurations to facilitate such operation. In the case of purely bipolar pulsed field delivery, distal portion 20 includes electrodes that form the bipolar configuration for energy delivery. A plurality of the electrodes 24 may serve as one pole while a second device containing one or more electrodes (not pictured) would be placed to serve as the opposing pole of the bipolar configuration. As shown in FIG. 1, the medical device 12 may be have a linear configuration with the plurality of electrodes 24. For example, the distal portion 20 may include six electrodes 24 linearly disposed along a common longitudinal axis 22. Alternatively, the distal portion 20 may include an electrode carrier arm that is transitionable between a linear configuration and an expanded configuration in which the carrier arm has an arcuate or substantially circular configuration. The carrier arm may include the plurality of electrodes 24 that are configured to deliver pulsed-field energy. Further, the carrier arm when in the expanded configuration may lie in a plane that is substantially orthogonal to the longitudinal axis of the elongate body 16. The planar orientation of the expanded carrier arm may facilitate ease of placement of the plurality of electrodes 24 in contact with the target tissue.

Figure 2:
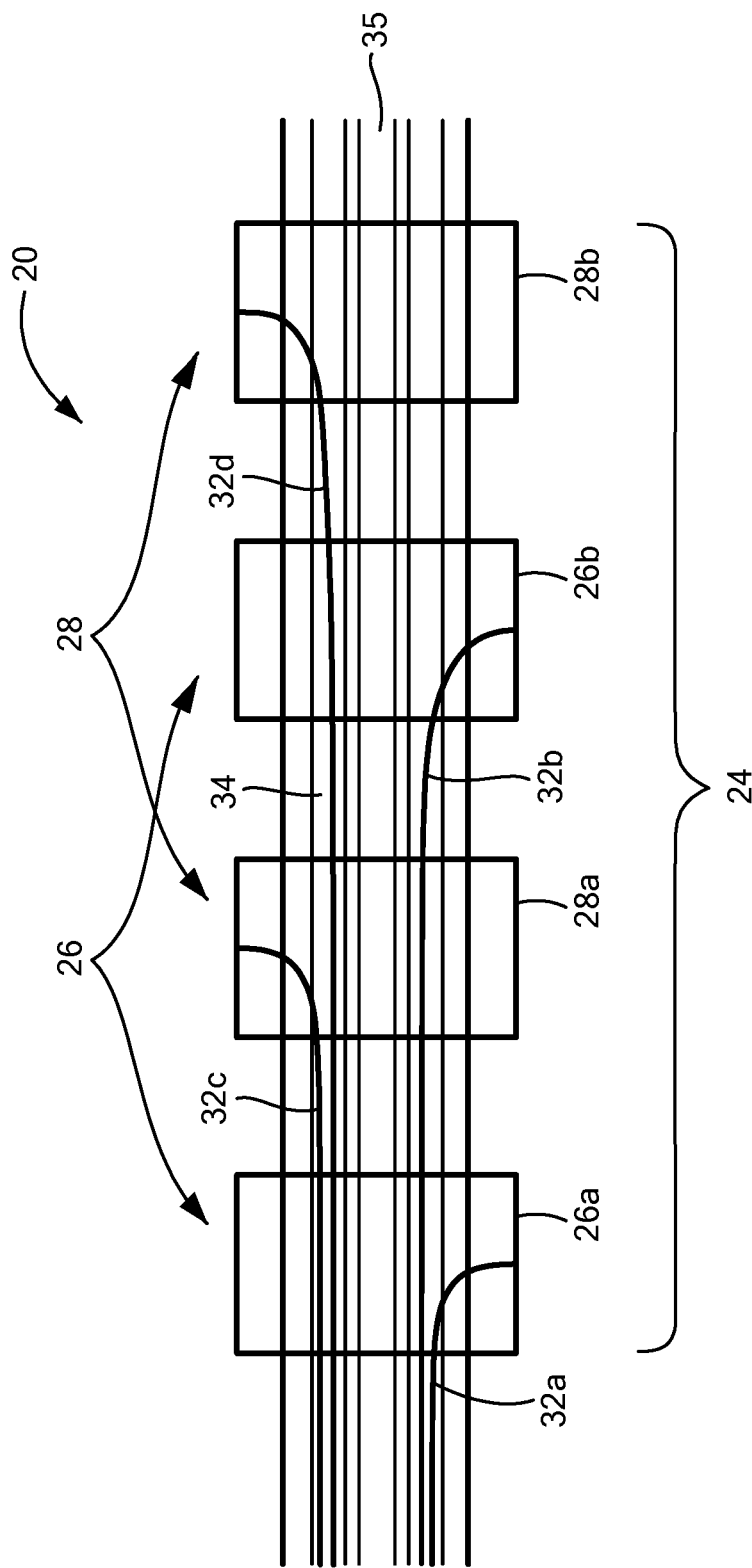
FIG. 2 is a side cross-section view of a distal portion of a medical device constructed in accordance with the principles of the present application.

Referring now to FIG. 2, in one configuration, the distal portion 20 includes the plurality of electrodes 24 in a linear configuration configured to deliver high voltage electroporation energy. The plurality of electrodes 24 includes a first electrode pair 26 having a first polarity, which may be fixed or variable, and a second electrode pair 28 having a second polarity different than the first polarity, which may be fixed or variable. For example, as shown in FIG. 2, the first electrode pair 26 includes a first electrode 26a and a second electrode 26b, although any number of electrodes are contemplated. That is, the pair of electrodes 26 and 28 refers to any two or more electrodes having the same polarity. The second electrode pair 28 includes a first electrode 28a and a second electrode 28b, although any number of electrodes are contemplated. In the configuration shown in FIG. 2, second electrode 28a is disposed between the first electrode 26a and the second electrode 26b and the second electrode 26 is disposed between the first electrode 28a and the second electrode 28b. The plurality of electrodes 24 may be evenly spaced along the distal portion 20 or alternatively may be spaced and non-uniform distances.

Continuing to refer to FIG. 2, a first lumen 30 extends through the distal portion 20. In the configuration shown in FIG. 2, the first lumen 30 is a discrete tube or channel that extends through the distal portion 20 toward the distal end of the device 12. The first lumen 30 includes a first conductor 32a configured to connect to the first electrode 26a of the first electrode pair 26 and a second conductor 32b configured to connect to the second electrode 26b of the first electrode pair 26. A second lumen 34 also extends through the distal portion 20. The second lumen 34 may be similarly constructed to that of the first lumen 30. In one configuration, the second lumen 34 is disposed on the opposite side of the distal portion 30 than that of the first lumen 30 but may be disposed in any location within the distal portion 20, for example, side-by-side or otherwise adjacent. The second lumen 34 includes a third conductor 32c configured to connect to the first electrode 28a of the second electrode pair 28 and a fourth conductor 32d configured to connect to the second electrode 28b of the second electrode pair 28. In the configuration shown in FIG. 2, the first lumen 30 and the second lumen 34 are parallel to each other. A guidewire lumen 35 may optionally be included in the medical device 12 and extending through the distal portion 20. In the configuration shown in FIG. 2, the guidewire lumen 35 is disposed between the first lumen 30 and the second lumen 34 and is parallel to both lumens. The guidewire lumen 35 may optionally be a lumen configured to house steering wires and more than one guidewire lumen 35 is contemplated to be included in the distal portion 20. In another configuration the channels may be comprised of insulated material around the designated conductors which themselves may be individually insulated; secured or freely floating in a common lumen or channel through the body of the medical device.

Figure 3:
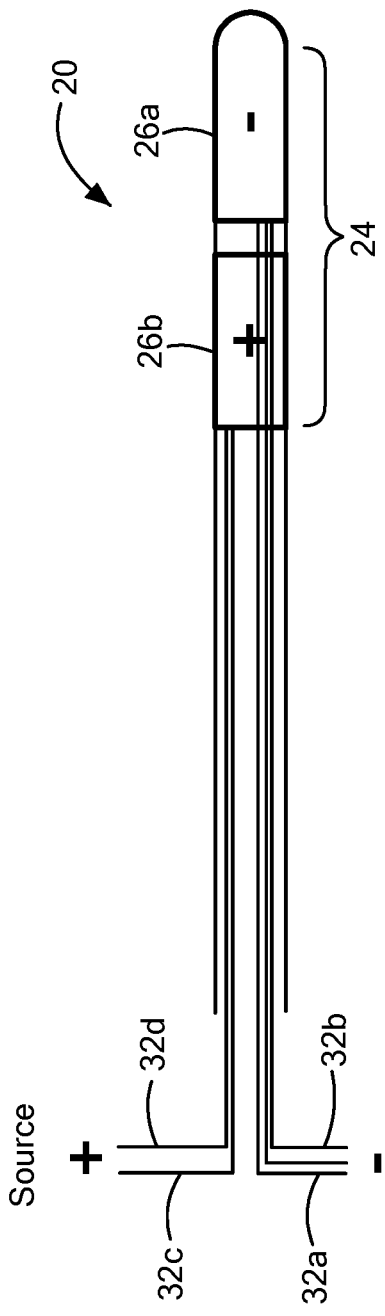
FIG. 3 is a side cross-section view of a distal portion of a medical device constructed in accordance with the principles of the present application.

Referring now to FIG. 3, in another configuration, the plurality of electrodes 24 includes the first electrode 26a and the second electrode 26b proximal to the first electrode 26a and are configured to deliver high voltage electroporation energy. Each of the first electrode 26a and the second electrode 26b includes two or more conductors coupled to each electrode as a redundancy. For example, as shown in FIG. 3, the first electrode 26a is coupled to the first conductor 32a and the second conductor 32b and the second electrode 26b is coupled to the third conductor 32c and the fourth conductor 32d or other conductors. In the configuration shown in FIG. 3, the conductors for each electrode extend along opposite sides of the distal portion 20 of the medical device 12. In the configuration shown in FIG. 3, the first electrode 26a and the second electrode 26 have fixed opposite polarities.

Figure 4:
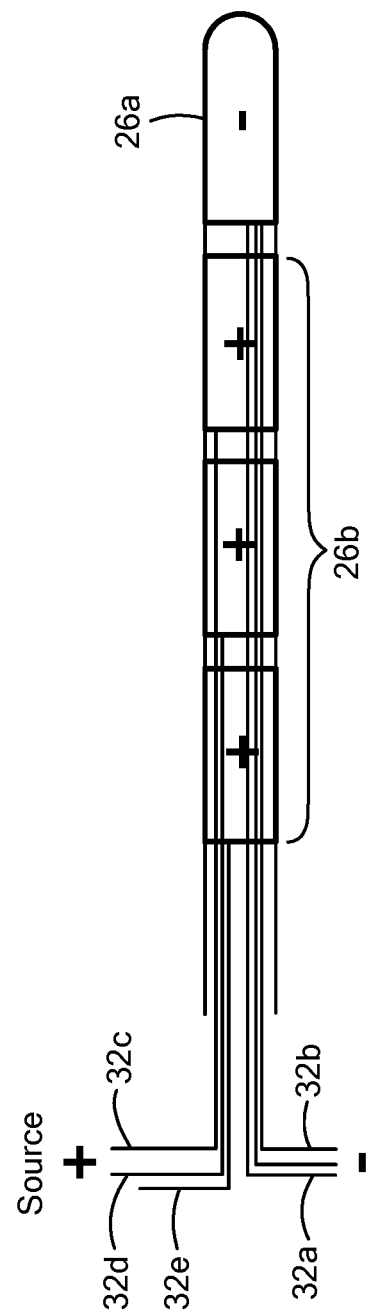
FIG. 4 is a side cross-section view of a distal portion of a medical device constructed in accordance with the principles of the present application.

Referring now to FIG. 4, in another configuration, the first electrode 26a is disposed at the distal end of the medical device 12 has a fixed polarity. In this configuration, the first electrode 26a includes the first conductor 32a and the second conductor 32b. The second electrode 26b includes a plurality of electrodes fixed at the same polarity opposite the polarity of the first electrode 26a. For example, as shown in FIG. 4, three second electrodes having a positive polarity are included along the distal portion 20 of the medical device 12. Each electrode of the second electrode 26b is coupled to a single conductor, for example, conductors 32c, 32d, and 32e each couple to one of the plurality of second electrodes 26b. Thus, in the event of failure of any one of the conductors coupled to the plurality of second electrodes 26, high voltage electroporation energy is still emitted in a bipolar manner as between the first electrode 26 and the remaining electrodes of the plurality of second electrodes 26b.

Figure 5A:
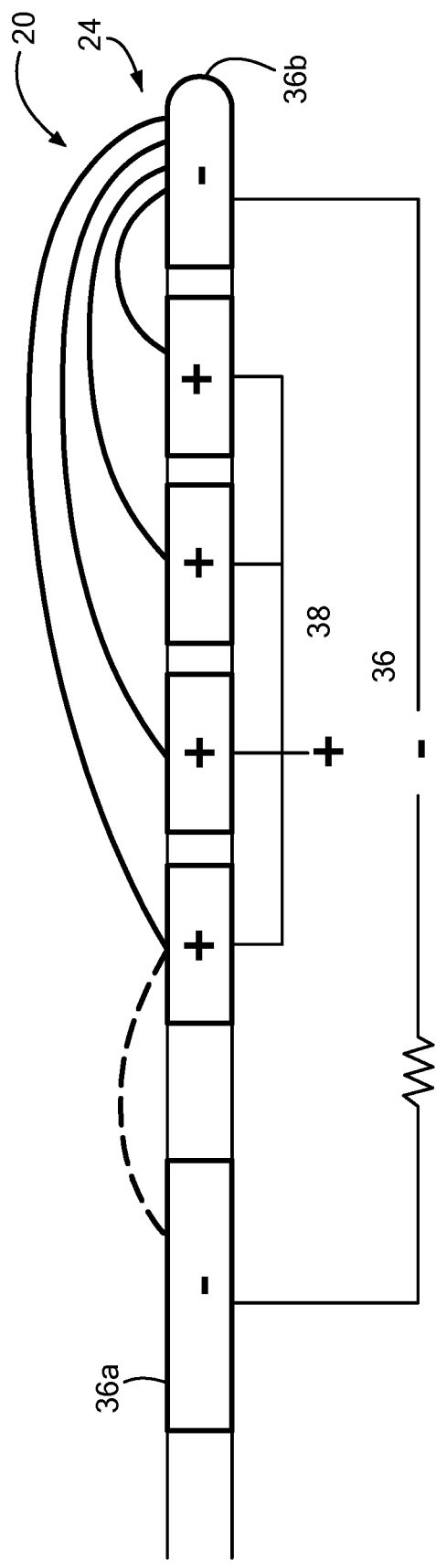
FIG. 5A is a side cross-section view of a distal portion of a medical device constructed in accordance with the principles of the present application and showing the energy transmission between electrodes.
Figure 5B:
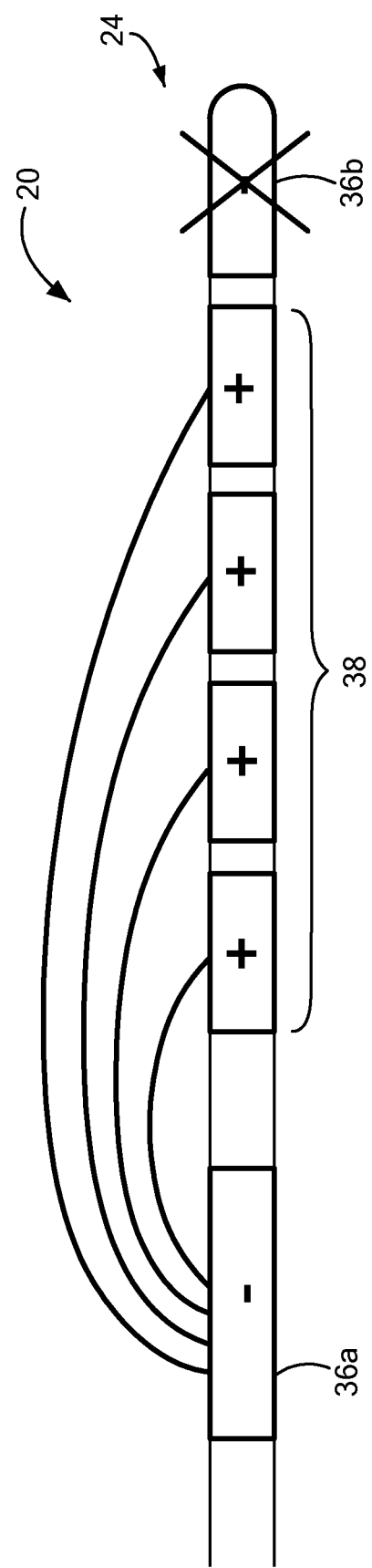
FIG. 5B is a side cross-section view of the distal portion of the medical device shown in FIG. 5A with a failure at the distal most electrode.

Referring now to FIGS. 5A and 5B, in another configuration, the plurality of electrodes 24 includes a first plurality of electrodes 36 along the distal portion 20. The first plurality of electrodes includes a first electrode 36a and a second electrode 36b distal to the first electrode 36a and disposed at the distal end of the distal portion 20. In this configuration, the first plurality of electrodes 36 has a first polarity, for example, negative. As shown in FIGS. 5A and 5B the first electrode 36a has a higher impedance path to the source polarity than the second electrode 36b. For example, the first electrode 36a may have a resistor or higher resistance wire path than the second electrode 36b. A second plurality of electrodes 38 is disposed between the first electrode 36a and the second electrode 36b. The second plurality of electrodes 38 has a second polarity different than the first polarity, for example, positive. A spacing between a distal most electrode of the second plurality of electrodes 38 and the second electrode 36b in this specific configuration is less than a spacing between the proximal most electrode of the second plurality of electrodes 38 and the first electrode 36a. Thus, in the event of a broken circuit path in the second electrode 36b during operation of the device 12, high voltage electroporation energy is transmitted in a bipolar manner between the first electrode 36a and the second plurality of electrodes 38, as shown in FIG. 5B.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   a catheter having a proximal portion and a distal portion;
   a plurality of electrodes disposed along the distal portion, the plurality of electrodes including a first electrode pair connected to a control system that delivers a first polarity to the first electrode pair through independent conductive pathways and a second electrode pair connected to the control system that delivers a second polarity to the second electrode pair through independent conductive pathways, the second polarity being different than the first polarity;
   a first lumen extending through the distal portion, the first lumen including a first conductor configured to connect to a first electrode of the first electrode pair and a second conductor configured to connect to a second electrode of the first electrode pair; and
   a second lumen extending through the distal portion and separated from the first lumen, the second lumen including a third conductor configured to connect to a first electrode of the second electrode pair and a fourth conductor configured to connect to a second electrode of the second electrode pair,
   wherein a conductive pathway that delivers the first polarity to the first electrode of the first electrode pair has a higher impedance than a conductive pathway that delivers the second polarity to the second electrode of the first electrode pair, the second electrode of the first electrode pair being disposed closer to a distal end of the medical device than the first electrode of the first electrode pair.

2. The device of claim 1, wherein the first electrode pair and the second electrode pair are configured to deliver electroporation energy.

3. The device of claim 1, further including a guidewire lumen extending through the distal portion.

4. The device of claim 3, wherein the first lumen and the second lumen are disposed on opposite sides of the guidewire lumen.

5. The device of claim 1, wherein the first electrode of the second electrode pair is disposed between the first electrode and the second electrode of the first electrode pair.

6. The device of claim 5, wherein the second electrode of the second electrode pair is disposed distal to the second electrode of the first electrode pair.

7. The device of claim 1, wherein the first lumen is parallel to the second lumen.

8. The device of claim 7, further including a guidewire lumen extending through the distal portion, and wherein the guidewire lumen is parallel to both the first lumen and the second lumen.

* * * * *